United States Patent
Zhao et al.

(10) Patent No.: US 12,329,434 B2
(45) Date of Patent: Jun. 17, 2025

(54) BALLOON CATHETER AND ELECTROPHYSIOLOGICAL SYSTEM

(71) Applicant: SHANGHAI MICROPORT EP MEDTECH CO., LTD., Shanghai (CN)

(72) Inventors: Qiancheng Zhao, Shanghai (CN); Bo Liang, Shanghai (CN); Yunzhu Xi, Shanghai (CN); Jiaqiang Jiang, Shanghai (CN); Yiyong Sun, Shanghai (CN)

(73) Assignee: SHANGHAI MICROPORT EP MEDTECH CO., LTD., Shanghai (CN)

( * ) Notice: Subject to any disclaimer, the term of this patent is extended or adjusted under 35 U.S.C. 154(b) by 977 days.

(21) Appl. No.: 17/427,497

(22) PCT Filed: Dec. 27, 2019

(86) PCT No.: PCT/CN2019/129030
§ 371 (c)(1),
(2) Date: Jul. 30, 2021

(87) PCT Pub. No.: WO2020/155978
PCT Pub. Date: Aug. 6, 2020

(65) Prior Publication Data
US 2022/0008111 A1   Jan. 13, 2022

(30) Foreign Application Priority Data

Jan. 31, 2019 (CN) .......................... 201910100650.6
Mar. 12, 2019 (CN) .......................... 201910182459.0

(51) Int. Cl.
*A61B 18/02* (2006.01)
*A61B 18/00* (2006.01)

(52) U.S. Cl.
CPC .... *A61B 18/02* (2013.01); *A61B 2018/00255* (2013.01); *A61B 2018/00577* (2013.01);
(Continued)

(58) Field of Classification Search
CPC ............................................. A61M 2025/1075
See application file for complete search history.

(56) References Cited

U.S. PATENT DOCUMENTS 5,395,361 A * 3/1995 Fox ....................... A61B 18/245
606/7
2002/0087156 A1 * 7/2002 Maguire ............. A61B 18/1492
606/41
(Continued)

FOREIGN PATENT DOCUMENTS

CN    101919729 A    12/2010
CN    204636708 U    9/2015
(Continued)

OTHER PUBLICATIONS

CN-204636708-U (Year: 2015).*

*Primary Examiner* — Ronald Hupczey, Jr.
(74) *Attorney, Agent, or Firm* — MUNCY, GEISSLER, OLDS & LOWE, P.C.

(57) ABSTRACT

A balloon catheter (100) and an electrophysiological system, which aim to improve the operability of accurately monitoring the balloon surface temperature at the surface of a double-layered balloon (110). The balloon catheter (100) comprises a catheter body (130), a double-layered balloon (110), at least one temperature measuring element (120), and at least one adhesion piece (140); the temperature measuring element (120) is disposed in an interlayer (113) formed by an inner layer balloon (112) and an outer layer balloon (111); the adhesion piece (140) is adheringly connected to the temperature measuring element (120), and is simultaneously adheringly connected to the inner layer balloon (112) or the (Continued)

outer layer balloon (111); the temperature measuring element (120) is attached to the inner layer balloon (112) or the outer layer balloon (111) by means of the adhesion piece (140); when the double-layered balloon (110) is deformed, the adhesion piece (140) may be displaced relative to the inner layer balloon (112) or outer layer balloon (111) connected to the adhesion piece (140), which enables the temperature measuring element (120) to be displaced relative to the inner layer balloon (112) or outer layer balloon (111) connected to the adhesion piece (140).

18 Claims, 7 Drawing Sheets

(52) U.S. Cl.
CPC ............... *A61B 2018/00797* (2013.01); *A61B 2018/00815* (2013.01); *A61B 2018/00821* (2013.01); *A61B 2018/0212* (2013.01); *A61B 2018/0262* (2013.01)

(56) References Cited

U.S. PATENT DOCUMENTS

| | | | |
|---|---|---|---|
| 2007/0219545 A1 | 9/2007 | Swanson | |
| 2009/0299178 A1* | 12/2009 | Kim | A61M 25/0009 600/435 |
| 2010/0069900 A1 | 3/2010 | Shirley et al. | |
| 2010/0318075 A1 | 12/2010 | Joye et al. | |
| 2011/0184398 A1* | 7/2011 | Desrochers | A61M 25/1011 606/21 |
| 2017/0105780 A1* | 4/2017 | Sara | A61B 18/02 |
| 2021/0009879 A1* | 1/2021 | Engler | C09J 183/04 |

FOREIGN PATENT DOCUMENTS

| | | |
|---|---|---|
| CN | 204655099 U | 9/2015 |
| CN | 105615998 A | 6/2016 |
| CN | 107411815 A | 12/2017 |
| CN | 108135645 A | 6/2018 |
| CN | 109646106 A | 4/2019 |
| EP | 2008624 A1 | 12/2008 |

\* cited by examiner

BALLOON CATHETER AND ELECTROPHYSIOLOGICAL SYSTEM

TECHNICAL FIELD

The present application relates to the field of medical instruments and, in particular, to a balloon catheter and an electrophysiology system.

BACKGROUND

Patients with atrial fibrillation are at very high risk for stroke. In atrial fibrillation, the atrium has a rapid and irregular beating and losses the contractility. This makes it easy for blood to stagnate in the atrium and form a thrombus. When the thrombus falls off and travels through the arteries to the brain, a stroke may occur. This can be treated by applying energy to the pulmonary vein for ablation via the interventional catheter to isolate the pulmonary vein potential. Hypertension is characterized by high prevalence, low awareness and significant harmfulness. Experimental data has suggested a correlation of hypertension to elevated renal sympathetic nerve excitability. Blocking the renal sympathetic nerves through ablation can not only lower blood pressure, but also benefit organ-specific chronic diseases arising from the hyperactivation of sympathetic nerve.

Ablation can be accomplished with a cryoballoon ablation, which is designed based on anatomical considerations and makes use of the contact between balloon and a target tissue for freezing. Cryoballoon ablation is characterized by the ability to form a continuous ablation within a single procedure. Specifically, the cryoballoon catheter having its distal end provided with a balloon and its proximal end connected to refrigerating installation is used. During the operation, a physician may places the catheter through a percutaneous puncture into the heart and reaches the pulmonary vein ostium. The balloon is then dilated and contact between an outer wall of balloon and myocardial tissue is adjusted. Then, a frozen liquid is sprayed from a liquid inlet pipe of the catheter directly onto an inner surface of the balloon. The frozen liquid instantly vaporizes and absorbs heat conducted from myocardial temperature to cool the tissue that is in contact with the balloon, thereby achieving cryoablation. Generally, the formation of an effective ablation focus requires maintaining the myocardial tissue at a low temperature for a sufficient time. To this end, temperature measuring elements is typically provided within the cryoablation balloon catheter, typically in the middle of the balloon, for monitoring an internal temperature of the balloon. The internal temperature is then used to estimate the temperature of the balloon surface. However, there is a possibility of a significant deviation between the estimated temperature and the actual temperature of the balloon surface, resulting in a low accuracy of the balloon surface temperature and thus directly affecting the ablation effect.

Various attempts have been made to provide temperature measuring elements on a balloon's surface to monitor the balloon surface temperature. However, this approach requires a high practicability. There exists no effective approach that is able to secure temperature measuring elements to a balloon surface while preventing the expansion and contraction of the balloon from being affected.

SUMMARY

An object of present application is to provide a balloon catheter and an electrophysiology system, in which the temperature measuring element is provided in the interlayer of the double layered balloon to enhance measuring accuracy of the balloon surface temperature; the adsorption element attaches the temperature measuring element to the inner or outer layer balloon, enabling to ensure that the temperature measuring element does not displaces during an normal ablation; and the adsorption element and the temperature measuring element are able to displace relative to the balloon along with the deformation of the balloon, avoiding any restraint on expansion and contraction of the balloon and thus raising practicability of balloon surface temperature monitor.

To achieve the above object, present application provides a balloon catheter comprising:
  a catheter body;
  a double layered balloon disposed at a distal end of the catheter body, the double layered balloon comprising an inner layer balloon and an outer layer balloon covering the inner layer balloon;
  at least one temperature measuring element disposed within a space between the inner and outer layer balloons; and
  at least one adsorption element absorbing and connecting both the temperature measuring element and the inner or outer layer balloon, so as to attach the temperature measuring element to the inner or outer layer balloon,
  wherein the adsorption element is displaceable relative to the inner or outer layer balloon to which the adsorption element is attached when the double layered balloon is deformed and also allows the temperature measuring element to displace relative to the inner or outer layer balloon to which the adsorption element is attached Optionally, the adsorption element is a physical adsorption element that is connected with the temperature measuring element via physical adsorption so as to allow the temperature measuring element to displace relative to the adsorption element when the double layered balloon is deformed, and is simultaneously connected with the inner or outer layer balloon via physical adsorption so as to allow the adsorption element to displace relative to the inner or outer layer balloon to which the adsorption element is attached when the double layered balloon is deformed and also to allow the temperature measuring element to displace relative to the inner or outer layer balloon to which the adsorption element is attached.

Optionally, a maximum displacement of the adsorption element relative to the inner or outer layer balloon to which the adsorption element is attached when the double layered balloon is deformed does not exceed 15% of an outer diameter of the double layered balloon in an expanded configuration.

Optionally, the adsorption element comprises a base and a physical absorption layer provided on the base.

A first part of the physical absorption layer physically absorbs the temperature measuring element, and a second part of the physical absorption layer physically absorbs one of the inner and outer layer balloons, the base configured to prevent the physical absorption layer from absorbing the other one of the inner and outer layer balloons.

Optionally, the physical absorption layer is made of a soft gel-like material that does not change its performance status before and after use.

Optionally, the material of the physical absorption layer is silicone or a hydrogel, and the base is a film made of a macromolecular material, the surface of which is coated with a physical absorption layer.

Optionally, at least one end of the adsorption element is fixed to one end of the double layered balloon.

Optionally, one end of the adsorption element is fixed to a proximal end of the double layered balloon, and the other end of the adsorption element is fixed to a distal end of the double layered balloon. A portion of the adsorption element between the proximal and distal ends of the double layered balloon absorbs and connects the temperature measuring element and simultaneously absorbs and connects the inner or outer layer balloon.

A length of the adsorption element is greater than a length of an unilateral contour line along the direction from the proximal to the distal ends of the double layered balloon in an expanded configuration.

Optionally, the adsorption element has a width that is greater than or equal to a maximum width of the temperature measuring element, so that the temperature measuring element is not exposed outside the adsorption element in its width direction.

Optionally, the adsorption element extends from one end of the temperature measuring element to the other end of the temperature measuring element so as to attach an entirety of the temperature measuring element to the inner or outer layer balloon.

Optionally, the adsorption element has a thickness of 100 μm or less and a width ranging from 0.2 mm to 3.0 mm.

Optionally, the temperature measuring element comprises two opposite ends and a main body between the two opposite ends.

At least one end of the temperature measuring element is fixed to one end of the double layered balloon, and at least part of the main body of the temperature measuring element is attached to the inner or outer layer balloon by the adsorption element.

Optionally, at least part of the main body is attached to the inner or outer layer balloon by a plurality of the adsorption elements.

Optionally, a plurality of the temperature measuring elements are provided and distributed at different locations in the space between the inner and outer layer balloons.

Optionally, the temperature measuring element is a linear-shaped temperature sensor that has at least one end fixed to one end of the double layered balloon and is arranged along a direction from a proximal end of the double layered balloon to a distal end of the double layered balloon.

Optionally, the adsorption element extends from the proximal to the distal ends of the double layered balloon so as to attach an entirety of the linear-shaped temperature sensor to the inner or outer layer balloon.

Optionally, the adsorption element is a long strip in shape.

Optionally, a portion of the temperature measuring element located between the proximal and distal ends of the double layered balloon are in an untensioned configuration when the double layered balloon does not expand, and wherein a length of the temperature measuring element in a stretched configuration is greater than a length of an unilateral contour line along the direction from the proximal to the distal ends of the double layered balloon in the expanded configuration.

Optionally, the linear-shaped temperature sensor is a thermocouple temperature sensor or thermistor temperature sensor.

Optionally, the temperature measuring element comprises a first wire, a second wire and a temperature sensing component, the first and second wires coupled to each other, the temperature sensing component disposed between the first and second wires. The temperature sensing component is configured to convert temperature information to electrical information, and the first and second wires is configured to transmit the electrical information.

The temperature sensing component is attached to the inner or outer layer balloon via a respective adsorption element and/or at least partial segments of at least one of the first and second wires are attached to the inner or outer layer balloon by a respective adsorption element.

Optionally, the catheter body comprises an outer tube and a core shaft disposed in the outer tube, a distal end of the core shaft extending out of the outer tube. The core shaft is connected to a distal end of the double layered balloon, and the outer tube is connected to a proximal end of the double layered balloon.

Optionally, the catheter body further comprises a fluid transfer pipe disposed between the core shaft and the outer tube, and the fluid transfer pipe is provided thereon fluid spraying orifices towards an surface of the inner layer balloon for spraying a cryogenic liquid into an interior of the inner layer balloon, the fluid spraying orifices arranged within a distal hemisphere of the double layered balloon.

To achieve above object, present application also provides an electrophysiology system comprising the above balloon catheter, an ablation energy output device and a control device. The ablation energy output device is in communication with the balloon catheter to provide the balloon catheter with an ablation medium, and the control device is configured to control the ablation energy output device to adjust a temperature of the ablation medium based on temperature information detected by the temperature measuring element so as to maintain a temperature of a surface of the double layered balloon within a predetermined ablation temperature range.

Compared with the prior art, the balloon catheter and electrophysiology system provided in present application offers the following advantages:

Firstly, the balloon catheter of present application comprising a double layered balloon that has an interlayer, at least one temperature measuring element provided in the interlayer in order to accurately detect an outer surface temperature of the double layered balloon. Therefore, in practical ablation process, the temperature measuring element is able to obtain more accurate temperature information of the lesion to improve the ablation effect. Moreover, in the balloon catheter of present application, in order to prevent the expansion and contraction of the double layered balloon from being affected by the temperature measuring element, the adsorption element is adopted to attach the temperature measuring element to a balloon surface. Through adsorption capacity of the adsorption element, the adsorption element is able to displace relative to the balloon along with the material deformation on the balloon surface when the double layered balloon expands and contracts. Since the temperature measuring element is attached to the inner or outer layer balloon by the adsorption element, the temperature measuring element is also displaceable relative to the balloon or the adsorption element. In this way, the temperature measuring element is able to comply with the expansion or contraction of the balloon well and not impact the balloon's expansion and contraction, thereby enabling to ensure efficiency and practicability of balloon surface temperature monitor. This also brings about other benefits: the diameter of an outer sheath through which the double layered balloon contraction can pass in a contracted configuration is reduced due to the uniform contraction of the double layered balloon; and a good contact between the double layered balloon and a target tissue is able to be achieved due to the uniform expansion of the balloon, which makes it possible for the temperature measuring element to obtain more accurate lesion temperature information and thus allows improving the ablation effect.

Secondly, the adsorption element of present application is preferably a physical adsorption element that physically absorbs the temperature measuring element to the balloon surface via the physical absorption layer. Since the physical absorption does not generate any substance that is detrimental to the balloon, there is no influence on balloon's strength, which ensures the safety of balloon operations. Moreover, the physical absorption involves surface-to-surface contact featuring a larger contact area compared to the local dispensing fixation, which reduces the risk of falling off of the temperature measuring element and ensures the reliability of temperature measuring during a surgical procedure.

Thirdly, the maximum displacement of the adsorption element relative to the double layered when the double layered balloon is deformed is preferred not exceeding 15% of the outer diameter of the double layered balloon in an expanded configuration, thereby allowing preventing the adsorption element and the temperature measuring element from displacing excessively relative to the balloon and thus allowing ensuring the validity of the balloon outer surface temperature monitor. More preferably, at least one end of the adsorption element is fixed to one end of the double layered balloon, which further prevents excessive axial displacement of the adsorption element.

Fourthly, the adsorption element preferably has a minimum width that is greater than or equal to a maximum width of the temperature measuring element, so that the temperature measuring element is not exposed outside the adsorption element in its width direction. This enables to avoid detachment of the temperature measuring element from the adsorption element and allows obtaining a higher practicability of balloon outer surface temperature monitor.

Fifthly, a plurality of temperature measuring elements are preferably provided and distributed at different locations in the double layered balloon's interlayer. This enables to achieve multiple-point temperature measurements of a target tissue that contacts with the balloon and helps to confirm contact conditions between the balloon and the target tissue, so as to further improve the ablation effect.

Sixthly, the catheter body in present application comprises the fluid transfer pipe and the fluid spraying orifices are disposed on the fluid transfer pipe for spraying a cryogenic liquid into an interior of the inner layer balloon to achieve the cryoablation. The fluid spraying orifices are preferably arranged within a distal hemisphere of the double layered balloon, enabling to utilize energy more efficient to save energy.

BRIEF DESCRIPTION OF THE DRAWINGS

In order to more clearly explain embodiments of present application or technical solutions of the prior art, the accompanying drawings needed to be used in the description of the embodiments or the prior art will be briefly introduced below. Apparently, these drawings in the following description merely show some embodiments of present application, and those of ordinary skill in the art can obtain other drawings in light of those contained drawings, without paying any creative effort.

In the figures, 1, temperature measuring element; 2, balloon;

100, balloon catheter; 110, double layered balloon; 111, outer layer balloon; 112, inner layer balloon; 113, interlayer; 120, temperature measuring element; 121, first wire; 122, second wire; 123, temperature sensing component; 130, catheter body; 131, fluid transfer pipe; 132, helical structure; 133, outer tube; 134, core shaft; 135, soft tip; 136, radiopaque marker; 140, adsorption element; 141, base; 142, physical absorption layer; 150, control handle; 151, electrical input/output interface; 152, fluid inlet interface; 153, lumen interface;

200, ablation energy output device; 300, control device.

DETAILED DESCRIPTION

As discussed in the background section, various attempts have been made so far to arrange temperature measuring elements such as fiber-optic or flexible printed sensors on a balloon's outer surface to monitor its outer surface temperature. However, due to the poor ductility, these temperature measuring elements have a low compliance with the balloon and are difficult to retain, which result in problems of breakage of these temperature measuring elements and non-uniform expansion or contraction of the balloon. Therefore, attempts of providing temperature measuring elements on the balloon's surface lack practicability. To this end, the inventors have made an attempt to arrange temperature measuring elements in the interlayer of a double layered balloon (i.e., the interlayer is a space between the inner and outer layers of the balloon) to monitor the balloon's outer surface temperature and retain them on the outer layer using a liquid adhesive. This attempt was found to still suffer from the following deficiencies.

Figure 1:
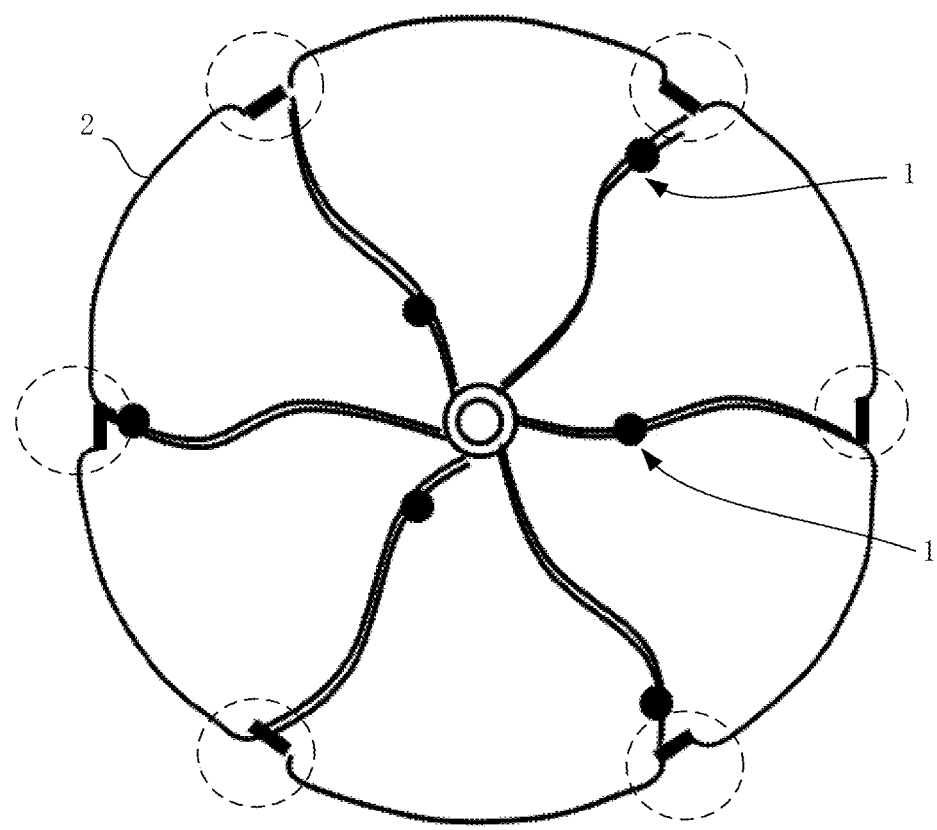
FIG. 1 diagram schematically illustrating how a balloon is restrained when it is expanding in accordance with an embodiment of the present application.

Firstly, after curation of the liquid glue, the fixed connection between the temperature measuring elements and the balloon surface is formed at the glue bonding position, making it impossible for the temperature measuring elements to displace relative to the balloon. As a result, as shown in FIG. 1, when the balloon expands, the temperature measuring elements 1 cannot comply themselves with the balloon 2 due to its own poor ductility (the temperature measuring elements generally consist of sensors and metal wires, or flexible circuit boards containing sensors). Consequently, the temperature measuring elements 1 either restrain the balloon 2 to result in the failure of uniform expansion of the balloon 2 and thus the formation of depressions on balloon surface, such as the areas circled by the dotted lines, or tighten the balloon 2 to create traces in the areas circled by the dotted lines. These would cause damages to the balloon and lower accuracy of balloon surface temperature measurement. Additionally, the temperature measuring elements 1 are prone to breakage, resulting in failure of the temperature measuring elements, which affects ablation procedure.

Secondly, the glue is composed of multiple chemical components. In practical use, the glue cures and thus adheres to a base. However, during the curation, the chemical components permeate into a surface layer of the adhered base. The permeation of chemical components may have a negligible influence on the base with a certain thickness. However, for the balloon with a small wall thickness of, e.g., 20-60 μm, the permeations of the chemical components into the surface layer of the balloon could weaken the balloon and render it less safe in surgical use.

In addition, the inventors have also attempted to fix temperature measuring elements to a balloon's surface by means of local dispensing. However, this approach thickens and hardens the balloon at the dispensing locations and causes the glue to firmly and integrally adhere to the balloon, which eventually creates significant strength differences between portions of the balloon with and without glue. Therefore, the balloon tends to be distorted (that is, the balloon cannot expands normally at the balloon area with glue, leading to the formation of depressions, as shown in FIG. 1) to affect ablation during normal ablation process. Likewise, the balloon also cannot contract uniformly (that is, bumps are formed at the balloon portions with glue after contraction), which is not favorable to the delivery and withdrawal of the balloon. For example, the uniform contraction would significantly raise the difficulty of the passage of the balloon through the outer sheath that is served as the channel for intravenously delivering the balloon into the heart lumen. Furthermore, the local dispensing typically has small contact areas with the temperature measuring elements, making it easy for them to fall off from the balloon or displace relative to the balloon and thus making the catheter less reliable in the procedure.

In view of the above, the present application proposes a balloon catheter including a catheter body, a double layered balloon, at least one temperature measuring element and at least one adsorption element. The catheter body includes an outer tube and a core shaft disposed in the outer tube. A distal end of the core shaft extends out of the outer tube. The double layered balloon is disposed at a distal end of the catheter body and includes an inner layer balloon and an outer layer balloon covering the inner layer balloon. A distal end of the double layered balloon is connected to the core shaft, and a proximal end of the double layered balloon is connected to the outer tube. The temperature measuring element is disposed within an interlayer formed by the inner and outer layer balloons. The adsorption element absorbs and connects both the temperature measuring element and the inner or outer layer balloon, thus attaching the temperature measuring element to the inner or outer layer balloon via the adsorption element. In practical use, when the double layered balloon expands or contracts, the adsorption element is displaceable relative to the inner or outer layer balloon to which it is attached and also allows the temperature measuring element to displace relative to the inner or outer layer balloon to which the adsorption element is attached. Of course, in present application, the maximum displacements of the adsorption element and the temperature measurement element relative to the balloon are such small that almost no impact is occurred on temperature measurements. Thus, effective monitor of the balloon's surface temperature can be achieved.

Therefore, it is possible to achieve relative accurate temperature information of the lesions to improve ablation effect by using the temperature measuring element arranged in the interlayer of the double layered balloon to detect temperature information of the outer surface of the double layered balloon. Moreover, the temperature measuring element is attached to the balloon surface with the adsorption elements. On one hand, this allows ensuring the temperature measuring element keeping stationary relative to the balloon when the balloon does not deform. On the other hand, this allows a certain displacement of the adsorption element relative to the balloon to which it is attached when the balloon deforms and hence allows a certain displacement of the temperature measuring element relative to the balloon. In this way, a better compliance of the temperature measuring element with the expansion and contraction of the balloon is able to be obtained and the non-uniform expansion and contraction of the balloon caused by the restraint is able to be avoided, which eventually improves practicability and reliability of balloon outer surface temperature monitor. Furthermore, the uniform contraction of the balloon reduces the diameter of the outer sheath through which the balloon catheter passes, which is favorable to the implementation of an interventional operation and raises the operation success rate.

The present application will be described in greater detail with reference to the accompanying drawings so that the invention will become more apparent and readily understood. Of course, the present application is not limited to the following specific examples, and general replacements well known to those skilled in the art are also embraced within the scope thereof. Additionally, while the present application is described in detail with reference to schematic figures, these figures are presented only for the purpose of facilitating the detailed description of the examples rather than limiting present application in any sense.

As used herein, the terms "proximal" and "distal" describe relative orientations, relative positions and directions between elements or actions, viewed by a physician operating the product. Without wishing to be limiting, a "proximal end" usually refers to an end of the product close to the physician during normal operation, while a "distal end" usually refers to an end thereof that enters the patient's body first. As used in the specification, and in the appended claims, the singular forms "a", "an" and "the" include plural referents unless the context clearly dictates otherwise. As used in the specification, and in the appended claims, the term "or" is employed in the sense including "and/or" unless the context clearly dictates otherwise. Further, the term "circumferential" generally refers to a direction around an axis of a double layered balloon.

Figure 2:
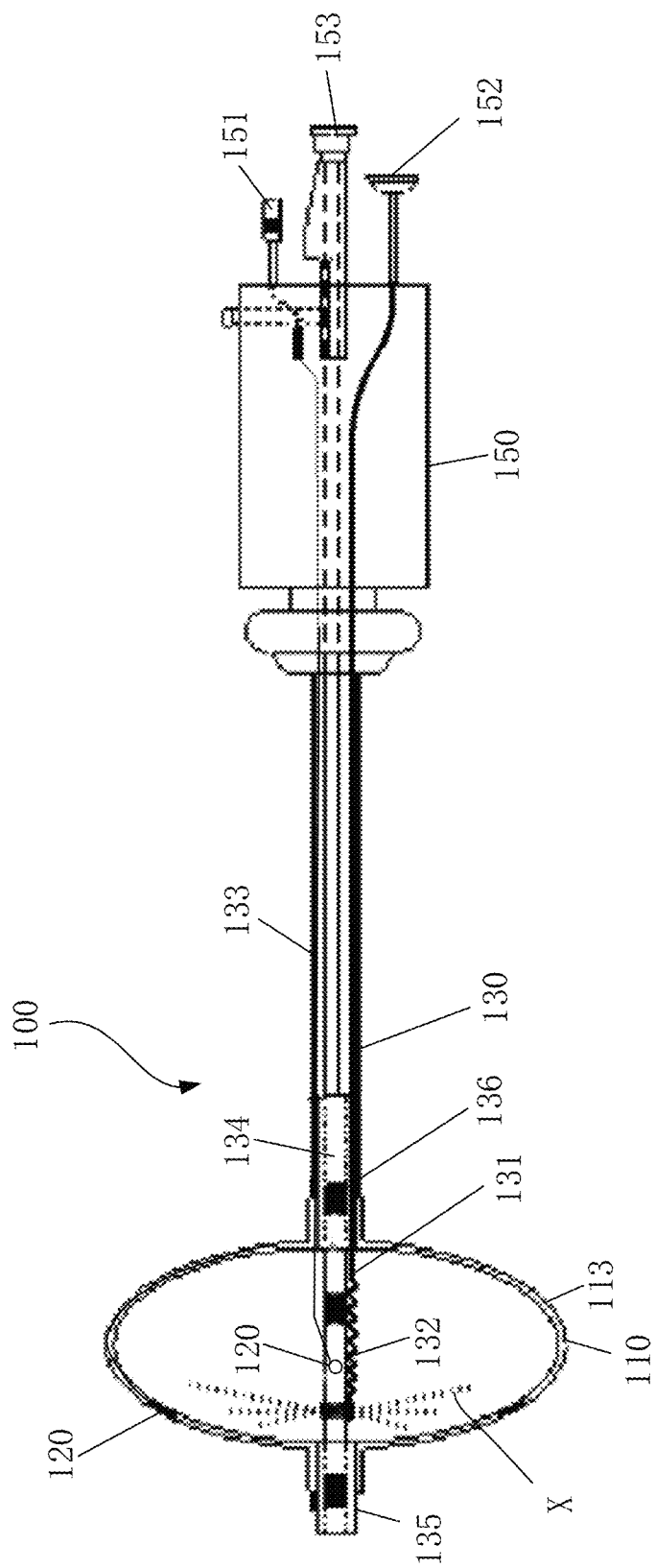
FIG. 2 is a main view of a balloon catheter according to an embodiment of the present application.
Figure 3:
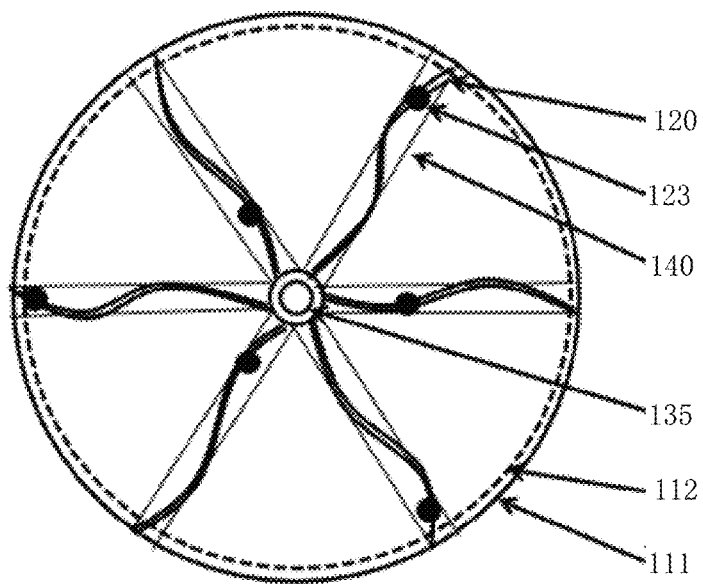
FIG. 3 is a left view of the balloon catheter of FIG. 2.
Figure 4:
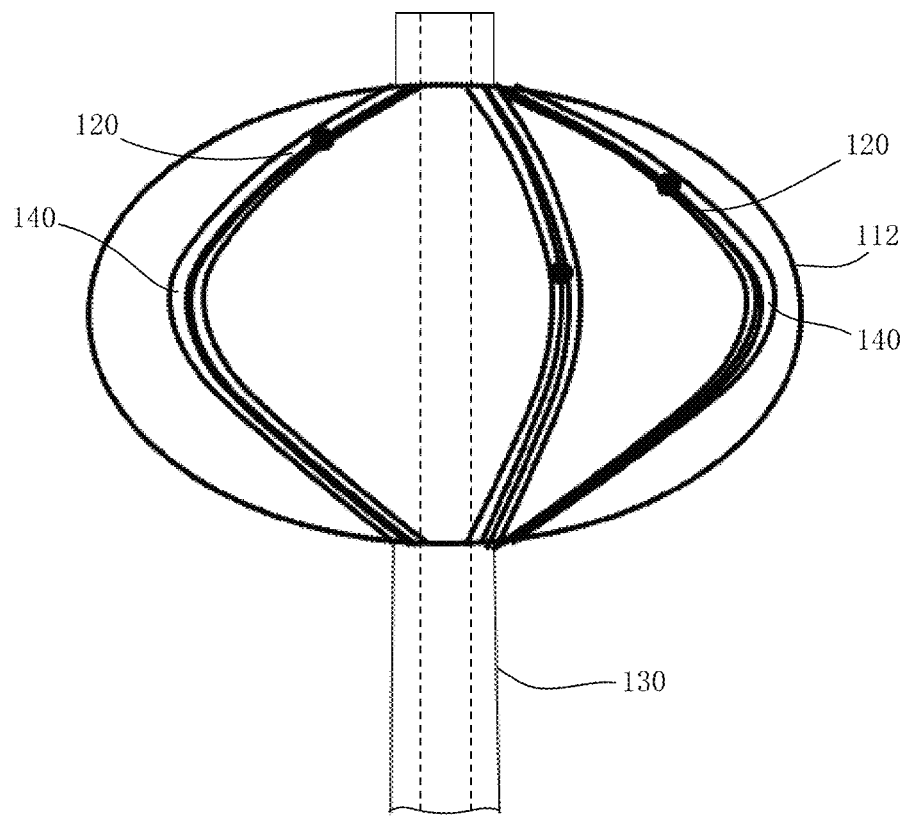
FIG. 4 is a schematic diagram of a distal end portion of a balloon catheter according to an embodiment of the present application.

Referring to FIGS. 2 to 4, an embodiment of present application provides a balloon catheter 100 including a double layered balloon 110, a temperature measuring element 120, a catheter body 130 and an adsorption element 140. The double layered balloon 110 is disposed at a distal end of the catheter body 130 and a part of the catheter body 130 is located in the double layered balloon 110 for spraying an ablation medium onto the double layered balloon 110. Here, examples of the ablation medium may include, but are not limited to, a cryogenic liquid.

In particular, the catheter body 130 includes an outer tube 133 and a core shaft 134 disposed within the outer tube 133. A distal end of the core shaft 134 extends out of the outer tube 133 and coupled to the distal end of the double layered balloon 110. A proximal end of the double layered balloon 110 is connected to the outer tube 133.

The double layered balloon 110 particularly includes an outer layer balloon 111 and an inner layer balloon 112 wrapped by the outer layer balloon 111. Proximal and distal ends of each of the outer layer balloon 111 and the inner layer balloon 112 are fixed to the catheter body 130. Both the outer and inner layer balloons 111, 112 are expandable. For example, a cryogenic liquid is sprayed into an interior space delimited by the inner layer balloon 112 at the distal end of the catheter body 130. The cryogenic liquid instantly vaporizes to expand by absorbing heat from human tissues, so as to result in the expansion of the inner layer balloon 112. When the inner balloon 112 expands, the outer balloon 111 expands under the action of the inner balloon 112. In this embodiment, the double layered balloon 110 may be formed of a material selected from polyesters, polyurethanes, thermoplastic elastomers, polyethylene, polyolefin copolymers or other suitable polymer materials, or from various combinations thereof.

At least one temperature measuring element 120 is provided and is disposed in the interlayer 113 formed by the inner layer balloon 112 and the outer layer balloon 111. Since the temperature measuring element 120 is capable of detecting temperature information of a surrounding region and the temperature measuring element 120 is disposed in the interlayer 113 formed by the inner layer balloon 112 and the outer layer balloon 111 while the space delimited by the inner balloon 112 and the outer balloon 111 is close to the outer surface of the double layered balloon 110, it is able to estimate the temperature information of the outer surface of the double layered balloon 110 more accurately when the temperature information detected by the temperature measuring element 120 is used to estimate the temperature information of the outer surface of the double layered balloon 110, thereby enabling to improve ablation effect.

According to a preferred embodiment of the present application, the temperature measuring element 120 is attached to the inner layer balloon 112 or to the outer layer balloon 111 through the adsorption element 140. For example, as shown in FIG. 4, the temperature measuring element 120 is attached to an outer surface of the inner layer balloon 112 through the adsorption element 140, so that the temperature measuring element 120 is able to monitor the temperature at a predetermined location of the double layered balloon 110. The adsorption performance of the adsorption element 140 enables the temperature measuring element 120 to comply with expansion and contraction of the double layered balloon 110. When the double layered balloon 110 expands or contracts, the adsorption element 140 is displaceable relative to the double layered balloon 110 with the deformation of the material of the balloon surface where the adsorption element 140 connects. Moreover, since the temperature measuring element 120 is attached to the inner 112 or outer 111 layer balloon via the adsorption element 140, the temperature measuring element 120 is also displaceable relative to the double layered balloon 110 or to the adsorption element 140. Of course, the displacement here is generally small (usually the maximum displacement does not exceed 5 mm) in value and almost no impact is imposed on the temperature measurement. Notably, the temperature measuring element 120 is also displaceable relative to the adsorption element 140.

Due to the relative displacements between the adsorption element 140 and the double layered balloon 110, between the adsorption element 140 and the temperature measuring element 120 and between the temperature measuring element 120 and the double layered balloon 110, constraints on the double layered balloon 110 during its expansion and contraction are avoided eventually, which enables the uniform expansion and contraction of the double layered balloon 110 and the improved practicability of the double layered balloon. In this way, the double layered balloon does not suffer either from impaired outer surface temperature monitor due to its non-uniform expansion, or from the breakage and failure of the temperature measuring element due to the poor ductility of the temperature measuring element. Further, the uniform contraction of the double layered balloon 110 enables to reduce diameter of the outer sheath through which the balloon catheter 100 passes, thereby facilitating the implementation of an interventional operation and improving the operation success rate.

It would be appreciated that in an normal ablation procedure of the double layered balloon 110, the adsorption element 140 maintains the temperature measuring element 120 stationary relative to the double layered balloon 110, so that the temperature measuring element 120 is capable of monitoring temperature at the predetermined location of the double layered balloon without any displacement. However, during the expansion of the double layered balloon 110 prior to the ablation procedure, the adsorption element 140 displaces relative to the double layered balloon 110 to allow the temperature measuring element 120 to comply with the expansion of the double layered balloon. This not only avoids any adverse impact on the double layered balloon's expansion but also lowers the risk of breakage of the temperature measuring element 120 due to its own poor ductility. Likewise, During contraction of the double layered balloon 110, the adsorption element 140 also displaces relative to the double layered balloon 110 to allow the temperature measuring element 120 to comply with the contraction of the double layered balloon, enabling the double layered balloon 110 to pass through the outer sheath successfully.

Further, the adsorption element 140 is preferred to be a physical adsorption element that connects both the temperature measuring element 120 and the inner layer balloon 112 through physical adsorption or connects both the temperature measuring element 120 and the outer layer balloon 111 through physical adsorption. It is just the physical absorption that allows the adsorption element 140 and hence the temperature measuring element 120 to displace relative to the double layered balloon 110 during the expansion and contraction of the double layered balloon 110. Specifically, due to the physical absorption of the adsorption element 140 to the temperature measuring element 120, the adsorption element 140 is able to displace relative to the temperature measuring element 120 when the double layered balloon 110 deforms. Meanwhile, since the adsorption element 140 also physically absorbs the balloon surface, the adsorption element 140 is also able to displace relative to the balloon surface to which it is attached when the double layered balloon 110 deforms. Thus, the temperature measuring element 120 is displaceable relative to the balloon surface to which the adsorption element is attached eventually.

Notably, the term "physical absorption" used herein differs from chemical absorption. Physical absorption only relies on the force between the adsorbent material and the adsorbed substrate surface to achieve physical bonding, where the adsorbent material slightly slide relative to the adsorbed substrate surface when the adsorbed substrate surface deforms relative to adsorbent material.

Figure 5:
FIG. 5 is a schematic diagram of an adsorption element according to an embodiment of the present application.

Furthermore, referring to FIG. 5, the adsorption element 140 preferably includes a base 141 and a physical absorption layer 142 arranged on the base 141. The physical absorption layer 142 may be directly applied to a surface of the base 141. In practical use, a first part of the physical absorption layer 142 on the adsorption element 140 physically absorbs the temperature measuring element 120, and a second part of the physical absorption layer 142 absorbs the inner 112 or outer 111 layer balloon. As an example, the adsorption element 140 is a tape with a physical absorption layer 142 coated on one surface thereof. The temperature measuring element 120 is bonded to the balloon surface directly with the tape. Then, the connection between the temperature measuring element 120 and the balloon surface can be achieved. It would be appreciated that, the effects brought by the physical absorption are that, the physical absorption layer 142 can firmly adhere the temperature measuring element 120 on the balloon surface when the balloon surface to which the adsorption element 140 is connected does not deform; and the physical absorption layer 142 slides along with the extension or contraction of the balloon surface material when the balloon surface extends or contracts, so that neither the adsorption element 140 nor the temperature measuring element 120 will affect the expansion or contraction of the balloon.

In embodiments of the present application, the physical absorption layer 142 is preferably made of a soft gel-like material that does not experience status changes in properties before and after use. Examples of the soft gel-like material may include silicone, hydrogels and so on, but the present application is not so limited, because other functionally similar soft gel-like materials are also applicable. In particular, in order to create physical adsorption, the chosen materials are required to keep their hardness unchanged before and after use (after use, adsorption with the surface of the substrate to be bonded is formed). For example, when silicone is used, it always keeps its soft status without any change in hardness before and after the absorption with balloon surface. Thus, according to the present application, the physical adsorption differs from the chemical adsorption element that experiences status changes in properties before and after use. For chemical adsorption, such as the glue that experiences status changes in properties before and after use, the status of the glue remarkably changes in properties after and before its adhesion with balloon surface, i.e., the status of the glue changes from the liquid before use to the solid after use and the hardness of the glue increases after use. If the glue is used to bond the balloon surface, the fixed connection is formed such that the balloon cannot displace relative to the attached element, affecting expansion and contraction of the balloon. Of course, in addition to the above effects, the physical adsorption will not produce substances that have an adverse effect on the balloon. For the double layered balloon with a thin wall-thickness, physical adsorption would not lower the strength of the balloon, enabling to ensure the operation safety. Furthermore, since both the temperature measuring element 120 and the adsorption element 140 are provided in the interlayer 113 of the double layered balloon 110, they are not easy to fall off because in addition to the protection provided by the outer layer balloon 111, the interlayer 113 itself is almost in a vacuum state. Thus, when the double layered balloon 110 contacts with and slides relative to a human tissue, the interlayer 113 is substantially not affected by external forces, avoiding sliding movement of the adsorption element 140 due to insufficient bonding force from physical adsorption.

Further, in embodiments of the present application, the maximum displacement of the adsorption element 140 relative to the double layered balloon 110 to which the adsorption element is attached when the double layered balloon is deformed preferably does not exceed 15% of the outer diameter of the double layered balloon 110 in an expanded configuration. For example, when the outer diameter of the double layered balloon 110 in an expanded configuration is 28 mm, the maximum displacement of the adsorption element 140 relative to the double layered balloon 110 may not exceed 4.2 mm.

Specifically, prior to the expansion of the double layered balloon 110, the adsorption element 140 may be stationary relative to the double layered balloon 110. At this time, as stated in a more concrete way, there are several points in the adsorption element 140 coincide with respective points on the surface of the double layered balloon 110 without any relative displacement. In this way, when the double layered balloon 110 expands, the adsorption element 140 displaces relative to the double layered balloon 110, causing the several points in the adsorption element 140 to displace relative to the respective points on the surface of the double layered balloon. Therefore, in present application, the displacement for two originally overlapping points before and after expansion is defined as the displacement of the adsorption element 140 relative to the double layered balloon 110, and the maximum displacement of the adsorption element 140 relative to the double layered balloon 110 is limited as not exceeding 15% of the outer diameter of the double layered balloon 110 in an expanded configuration.

For ease of understanding, taking the first point on the adsorption element 140 coinciding with the second point on the outer surface of the inner balloon 112 before expansion of the double layered balloon 110 as an example to describe the displacement of present application in detail. The first point coincides with the second point before expansion of the double layered balloon 110. When the double layered balloon 110 starts to expand, the first point displaces relative to the second point and non-coincidence between the first and second point occurs. At this time, the distance between the first and second points along the outer surface of the expanded inner layer balloon 112 is defined as the displacement of the first point relative to the second point. Regardless of whether the adsorption element 140 is attached to the double layered balloon 110 either at one end or at both ends, the same definition of displacement of the adsorption element 140 relative to the double layered balloon 110 applies.

It would be appreciated that the maximum displacement of the adsorption element 140 relative to the double layered balloon 110 is generally related to the expansion properties of the selected double layered balloon 110. In other words, those of ordinary skill in the art may choose the balloon with corresponding properties to meet the requirement that the maximum displacement of the adsorption element 140 relative to the double layered balloon 110 does not exceed 15% of the outer diameter of the double layered balloon 110 in the expanded configuration. In addition, it would be appreciated that, as detailed below, fixing one or both ends of the adsorption element 140 to the double layered balloon 110 is able to advantageously reduce displacement of the adsorption element 140 relative to the double layered balloon 110 when the double layered balloon expands. This advantage is provided as an improvement for the advantage that a maximum displacement of the adsorption element 140 does not exceed 15% of the outer diameter of the double layered balloon 110 in the expanded configuration. Furthermore, it would be also appreciated that the displacement is not limited to any particular direction.

Additionally, the base 141 is preferred to be a thin film made of a polymeric material such as polyimide or polyester for isolating the physical absorption layer 142 from the inner 112 or outer 111 layer balloon that is not attached to the adsorption element 140. For example, if the adsorption element 140 is attached to the inner layer balloon 112, then the base 141 is configured to isolate the physical absorption layer 142 from the outer layer balloon 111. Alternatively, if the adsorption element 140 is attached to the outer layer balloon 111, then the base 141 is configured to isolate the physical absorption layer 142 from the inner layer balloon 112. In this way, the physical absorption layer 142 is prevented to absorb the outer layer balloon 111 or the inner layer balloon 112 to affect expansion and contraction of the balloon.

In an exemplary embodiment, the adsorption element 140 is composed of a thin film and a soft gel-like material disposed on one side of the thin film. In practical use, the temperature measuring element 120 is placed, for example, on the outer surface of the inner layer balloon 112, and the adsorption element 140 is then directly bonded to both the temperature measuring element 120 and inner layer balloon 112 by physical absorption. Optionally, the adsorption element 140 has a thickness of 100 μm or less and a width in the range of from 0.2 mm to 3 mm. On the premise that the adsorption element 140 can absorb the temperature measuring element 120 sufficiently, the width of the adsorption element 140 should be as narrow as possible within this width range, so as to reduce the impact on balloon expansion. Optionally, the base 141 may have a thickness of 50 μm or less. Optionally, the physical absorption layer 142 may have a thickness of 75 μm or less.

Additionally, in embodiments of the present application, in order to avoid excessive axial displacement of the adsorption element 140 as a result of expansion or contraction of the double layered balloon, it is preferred that at least one end of the adsorption element 140 is fixed to a respective end of the double layered balloon 110. In some embodiments, one end of the adsorption element 140 is fixed to the proximal or distal end of the double layered balloon 110. In some embodiments, one end of the adsorption element 140 is fixed to the proximal end of the double layered balloon 110, while the other end is fixed to the distal end of the double layered balloon 110, as shown in FIGS. 3 and 4. In this way, a portion of the adsorption element 140 between the proximal and distal ends of the double layered balloon 110 physically absorbs both the temperature measuring element 120 and the inner 112 or outer 111 layer balloon. Here, it is to be noted that one end of the adsorption element being fixed to the double layered balloon refers to that one end of the adsorption element is maintained always stationary relative to the double layered balloon without any displacement. Of course, in practical use, two ends of the adsorption element 140 may be not fixed to the double layered balloon, so that the entire adsorption element 140 physically absorbs the temperature measuring element 120 and the double layered balloon 110.

Further, the adsorption element 140 extends from one end of the temperature measuring element 120 to the opposing end of the temperature measuring element 120 so that the whole temperature measuring element 120 is attached to the inner layer balloon 112 or the outer layer balloon 111. For example, as shown in FIGS. 3 and 4, the adsorption element 140 extends from the proximal to the distal end of the double layered balloon 110 so that the whole temperature measuring element 120 is attached to the inner 112 or outer 111 layer balloon along the axial direction of the balloon. This enables to better attach the temperature measuring elements 120 to the inner 112 or outer 111 layer balloon, so as to retain them on the inner 112 or outer 111 layer balloon. Moreover, in the case that the adsorption element 140 is fixed at both ends to the double layered balloon 110, the portion of adsorption element 140 between the proximal and distal ends of the double layered balloon is required to have a certain amount of elongation in length in order to not restrain the expansion of balloon by the adsorption element 140. Preferably, the minimum length of the adsorption element 140 (that is, the initial length of the adsorption element 140 that is not stretched) is greater than a length of an unilateral contour line along the direction from the proximal to the distal ends of the double layered balloon 110 in an expanded configuration, so as to avoid restrained expansion of the balloon due to an excessively short length of the adsorption element 140.

In some embodiments, the adsorption element 140 may be a long strip in shape, facilitating to cover the entire temperature measuring element 120 in the axial direction of the balloon with merely one adsorption element 140, which enables to achieve a more firm attachment of the temperature measuring element 120. In alternative embodiments, the adsorption element 140 may have other shapes such as square, rectangular, etc. The adsorption element 140 may attach either the whole or part of the temperature measuring element 120 to the balloon. Moreover, the width of the adsorption element 140 is preferably greater than or equal to a width of the temperature measuring element 120 so that the temperature measuring element 120 is not exposed outside the adsorption element 140 in the width direction of the temperature measuring element 120. This helps the adsorption element 140 completely covers the temperature measuring element 120 in the circumferential direction of the double layered balloon. Each of the adsorption element 140 and the temperature measuring element 120 may have a varying width. In this case, it is preferred that a minimum width of the adsorption element 140 is greater than or equal to a maximum width of the temperature measuring element 120, so that the temperature measuring element 120 is not exposed outside the adsorption element 140 along the width direction of the temperature measuring element 120. Herein, it is possible that only a portion of the adsorption element 140 that covers the temperature measuring element 120 has a minimum width greater than or equal to the maximum width of the temperature measuring element 120, while the rest portion of the adsorption element 140 that does not cover the temperature measuring element 120 may have a width lower than the temperature measuring element 120.

In an exemplary embodiment, the minimum length of the adsorption element 140 is equal to a length of the temperature measuring element 120. For example, the temperature measuring element 120 is a linear-shaped temperature sensor that is in an untensioned configuration before the balloon expands. In this case, the minimum length of the adsorption element 140 is equal to a stretched length of the temperature measuring element 120. This can ensure both that the adsorption element 140 is able to cover the entire temperature measuring element 120 in the axial direction of the double layered balloon and that the adsorption element 140 has a certain amount of elongation when the balloon expands without restricting the expansion of the balloon. Of course, the present application is not limited to embodiments in which each temperature measuring element 120 is connected to the double layered balloon by only one adsorption element 140. In alternative embodiments, each temperature measuring element 120 may be connected to the double layered balloon by a plurality of adsorption elements 140, for example, the plurality of adsorption elements 140 arranged and spaced apart along a length direction of the temperature measuring element 120. In this way, the temperature measuring element 120 may be bonded in multiple segments.

Further, the temperature measuring element 120 includes two opposing ends and a main body between the two ends. At least one end of the temperature measuring element 120 is fixed to a respective end of the double layered balloon 110. For example, in some embodiments, one end of the temperature measuring element 120 is fixed to the proximal or distal end of the double layered balloon 110. In some embodiments, as shown in FIGS. 3 and 4, one end of the temperature measuring element 120 is fixed to the proximal end of the double layered balloon 110, while the other end is fixed to the distal end of the double layered balloon 110. Additionally, at least part of the main body of the temperature measuring element 120 between the proximal and distal ends of the double layered balloon 110 is physically absorbed to the inner layer balloon 112 or the outer layer balloon 111 by the adsorption element 140, thereby further restricting excessive displacement of the temperature measuring element 120 along the circumferential direction of the balloon by the adsorption element 140.

With continued reference to FIGS. 3 and 4, the temperature measuring element 120 preferably has a linear shape and is preferably arranged along the axial direction of the double layered balloon 110. That is, the linear-shaped temperature sensor is arranged along the direction from the proximal end of the double layered balloon to the distal end thereof. More preferably, prior to the expansion of the double layered balloon 110, the main body of the temperature measuring element 120 between the proximal and distal ends of the double layered balloon 110 is in an untensioned configuration. After the expansion of the double layered balloon 110, the temperature measuring element 120 has a stretched length greater than the length of the unilateral contour line along the direction from the proximal to the distal ends of the double layered balloon in an expanded configuration. In this way, the temperature measuring element 120 is able to stretch to a certain extent during expansion of the balloon, so as to effectively avoid breakage of the temperature measuring element 120. Further, the physical absorption layer 142 will not exert any adverse impact on the stretching of temperature measuring element 120, making the temperature measuring element 120 to break even less likely.

Preferably, a plurality of temperature measuring elements 120 are provided and distributed at different locations in the interlayer 113. Preferably, they are uniformly distributed around the central axis of the inner layer balloon 112. In this embodiment, the plurality of temperature measuring elements 120 are able to detect temperature information of multiple locations. In ablation operations, the outer surface of the double layered balloon 110 typically has a spherical shape which usually cannot completely match the irregular, cylindrical shape of the lesion at one time, resulting in poor contact between the outer surface of the double layered balloon and the lesion. However, how well the double layered balloon 110 is matched with the lesion has a direct impact on the results of the ablation operation. Therefore, during the ablation operation, it is necessary to confirm whether full contact between the double layered balloon 110 and the lesion has been achieved. Due to blood circulation, any portion of the outer surface of the double layered balloon 110 in insufficient contact with tissue is washed by blood to cause its temperature significantly higher than that the temperature of any portion in good contact with the tissue. Therefore, various contact of the double layered balloon 110 with the tissue will lead to various temperatures of respective contact points of the double layered balloon 110. Therefore, in the balloon catheter 100 of this embodiment, the plurality of temperature measuring elements 120 distributed in the double layered balloon 110 are used to detect the temperature information at multiple locations. The detected temperature information is used to determine the contact of respective locations of the double layered balloon 110 with the tissues, which is served as a basis for further evaluation of the ablation result. Compared with the prior art where whether complete ablation of the lesion has been achieved by the balloon is observed through X-ray observation of the radiopaque agent, there is no necessity to perform radiographs multiple times on the balloon catheter 100 of the present application. That is, the patient would not be exposed to X-ray repeatedly, which is favorable to the patient's health. At the same time, the enhanced surgical efficiency and reduced surgical risk are able to be achieved.

Figure 6:
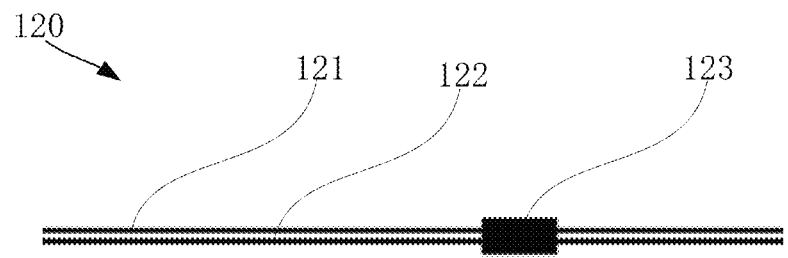
FIG. 6 is a schematic diagram of a temperature measuring element according to an embodiment of the present application, which is implemented as a thermocouple temperature sensor.

The linear-shaped temperature measuring element 120 may be a thermocouple temperature sensor as shown in FIG. 6. Alternatively, the linear-shaped temperature measuring element 120 may be a thermistor-based temperature sensor, as shown in FIG. 7.

As shown in FIG. 6, in this embodiment, the temperature measuring element 120 may include a first wire 121, a second wire 122 and a temperature sensing component 123. The first and second wires 121, 122 may be arranged in either a parallel or crossover configuration. The temperature sensing component 123 is disposed between the first and second wires 121, 122 as a temperature measuring point for detecting temperature information. The temperature sensing component 123 may also be configured to convert temperature information into electrical information, which is then transmitted by the first and second wires 121, 122. For example, the first wire 121 may be a copper wire, while the second wire 122 may be a constantan wire. The temperature sensing component 123 may be soldered to both a segment of the first wire 121 and a segment of the second wire 122. The conversion from temperature information to electrical information may occur at the soldered segments of the first and second wires 121, 122, and the converted electrical information may be sent out through the first and second wires 121, 122, so as to complete detection of temperature information at soldered segments of the first and second wires 121, 122. Therefore, the temperature information is detected by the thermocouple formed at the soldered segments of the first and second wires 121, 122 can be derived As shown in FIG. 7, in other embodiments, the temperature sensing component 123 may also be a thermistor that is electrically connected to both the first and second wires 121, 122. The first and second wires 121, 122 are formed as a twisted pair. In this embodiment, the temperature measuring element is implemented as a linear-shaped thermocouple or thermistor temperature sensor for the reason that these two temperature sensors are soft and not prone to breakage.

Figure 7:
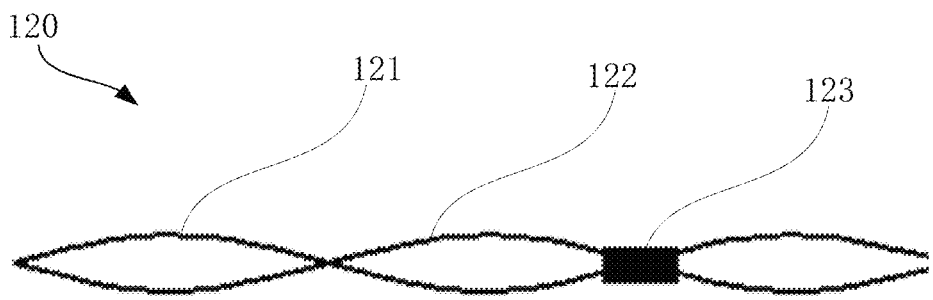
FIG. 7 is a schematic diagram of a temperature measuring element according to an embodiment of the present application, which is implemented as a thermistor temperature sensor.

With continued reference to FIGS. 6 and 7, the temperature sensing component 123 has a proximal side and a distal side. The first and second wires 121, 122 may be connected to the proximal side and then pass through the catheter body 130 via the third wire (not shown) to connect the electrical input/output interface 151 provided on a control handle 150, so as to send temperature information to the outside. The third wire may be an extension of both the first and second wires 121, 122, which is connected to the electrical input/output interface 151. Alternatively, the third wire may be a separate wire that connects the first and second wires 121, 122 to the electrical input/output interface 151. In this case, one end of the third wire is connected to both the first and second wires 121, 122, while the other end of the third wire is connected to the electrical input/output interface 151. Alternatively, two third wires may be provided, one of which connects the first wire to the electrical input/output interface 151 and the other one of which connects the second wire 122 to the electrical input/output interface 151. Preferably, at least one wire is connected to the distal side of the temperature sensing component 123 for fixing the distal end of the double layered balloon 110. However, the present application is not so limited, as any other suitable flexible member may be connected to the distal side, instead of the wire.

Further, in one embodiment of present application, only the temperature sensing component 123 is physically absorbed to a surface of the balloon via the adsorption element 140, and the proximal end of at least one of the first and second wires 121, 122 is fixed to the proximal end of the double layered balloon 110. Moreover, each of the first wire 121, the second wire 122 and the temperature sensing component 123 is disposed within the interlayer 113 delimited by the inner layer balloon 112 and the outer layer balloon 111. Since the adsorption element 140 physically absorbs each of the double layered balloon 110 and temperature sensing component 123, the temperature sensing component 123 is able to displace relative to the double layered balloon 110 and the adsorption element 140 during expansion and contraction of the balloon, thus enabling to comply the temperature sensing component 123 with the expansion and contraction of the double layered balloon 110 and avoiding the temperature sensing component 123 from breakage and failure due to its poor ductility. Further, in response to the expansion of the balloon, each of the first and second wires 121, 122 is able to stretch from its unstretched state and thus not restrain the expansion of the balloon.

In another exemplary embodiment, the adsorption element 140 may further physically absorb part of the first wire 121 and/or second wire 122 to the inner 112 or outer 111 layer balloon. In this case, the absorbed part of the first wire 121 and/or second wire 122 is movable relative to the double layered balloon 110 during the expansion and contraction of the balloon without forming a fixed connecting point. As a result, there is no restraint to the double layered balloon. In addition, as the temperature sensing component 123 is not fixedly connected to the balloon, it will not restrain the balloon as well.

In other exemplary embodiments, as shown in FIGS. 3 and 4, the adsorption element 140 physically absorbs the entire first wire 121 and/or second wire 122 to the inner 112 or outer 111 layer balloon. In this case, the entire first wire 121 and/or second wire 122 can move relative to the double layered balloon 110 during the expansion and contraction of the balloon without forming a fixed connecting point. As a result, there is no restraint to the double layered balloon. In addition, as the temperature sensing component 123 is not fixedly connected to the balloon, it will not restrain the balloon as well. For example, each of the first and second wires 121, 122 is fixed to the double layered balloon 110 at its proximal end and physically absorbed to the double layered balloon 110 by the adsorption element 140 throughout its entire length including the temperature sensing component 123. However, in alternative embodiments, the adsorption element 140 physically absorbs the first wire 121 and/or second wire 122 to the inner 112 or outer 111 layer balloon without physically absorbing the temperature sensing component 123 to the double layered balloon. In this case, expansion and contraction of the balloon will also not be restrained.

Of course, in other embodiments, the temperature measuring element 120 may be in another form such as, an optical fiber or a flexible printed sensor, and the present application is not limited to any particular form thereof.

Further, if a plurality of temperature measuring elements 120 are provided, it is preferred that at least some of the temperature sensing components 123 are arranged along different circumferences of the double layered balloon 110. That is, at least one temperature sensing components 123 is arranged on different circumferences of the double layered balloon. It is more preferred that, all temperature sensing components 123 are circumferentially spaced from one another when projected to a same circumference. For example, as shown in FIG. 3, six temperature sensing components 123 are circumferentially spaced, preferably equidistantly, from one another on the balloon, and distances from the six temperature sensing components 123 to the balloon's center may vary.

Further, in addition to arrange the temperature measuring element 120 in the interlayer 113, it is also possible to arrange the temperature measuring element 120 in other configuration. For example, at least one temperature measuring element 120 is arranged on a section of the catheter body 130 inside the inner layer balloon 112 in order to capture temperature information of the interior of the balloon, which is also connected to the electrical input/output interface 151 on the control handle 150 with wires. Of course, different temperature measuring elements 120 may be connected to a single electrical input/output interface 151. In this case, various data channels may be provided in the electrical input/output interface 151, through which respective temperature measuring elements 120 transmit data.

The structure of the catheter body 130 will be described in more detail below. Referring to FIG. 2, the catheter body 130 is a non-rigid structure that is bendable freely. Preferably, the catheter body 130 is made of a macromolecular material, such as a thermoplastic polyurethane (TPU) elastomer, block polyetheramide resin (Pebax) or nylon. The catheter body may be metal woven tube. Preferably, the proximal end of catheter body 130 is provided with the control handle 150 that is disposed on the outer tube 133. In particular, the control handle 150 may be configured to manipulate and control the bending of the catheter body 130.

The electrical input/output interface 151 is provided on the control handle 150, and the proximal end of the temperature measuring element 120 extends through the catheter body 130 to connect with the electrical input/output interface 151 so as to send the detected temperature information to external equipment. The control handle 150 further includes at least one fluid inlet interface 152, at least one fluid outlet interface (not shown) and at least one lumen interface 153. The lumen interface 153 is configured to introduce a guidewire, a mapping catheter, a radiopaque medium or other instruments. The fluid inlet interface 152 is in fluid communication with the fluid transfer pipe 131 in order to introduce an ablation medium from an external source into the balloon catheter 100. The fluid outlet interface is configured to exhaust the ablation medium or other media from the double layered balloon.

The catheter body 130 further includes a fluid transfer pipe 131 that is also sleeved within the outer tube 133, particularly between the outer tube 133 and the core shaft 134. The fluid spraying orifices (not shown) towards the surface of the inner layer balloon are provided on the fluid transfer pipe 131. The fluid spraying orifices are configured to spray the ablation medium X to the interior of the inner layer balloon 112. Herein, the ablation medium is not limited to a cryogenic liquid. Preferably, the fluid spraying orifices are arranged within a distal hemisphere of the double layered balloon 110 so as to be closer to, for example, a pulmonary vein orifice to be ablated. This allows enhanced utilization of cryogenic energy, leading to energy savings. More preferably, the cryogenic liquid may be carbon dioxide or nitrous oxide.

Additionally, as shown in FIG. 2, the fluid transfer pipe 131 particularly includes a distal helical structure 132 and a longitudinal extension in fluid communication with the helical structure 132. The longitudinal extension extends through the catheter body 130 and connects the fluid inlet interface 152. Preferably, a plurality of fluid spraying orifices are arranged on the helical structure 132 in order to spray the ablation medium towards various directions.

Additionally, the core shaft 134 is hollow and movably disposed in the outer tube 133. The control handle 150 is manipulated to allow the core shaft 134 to move within the outer tube 133, so as to achieve release from a sheath and retraction into the sheath of the double layered balloon 110. The proximal end of the core shaft 134 is in communication with the lumen interface 153 of the control handle 150 so as to allow passage of necessary instruments, such as guidewire, mapping catheter or radiopaque fluid. The catheter body 130 further includes a fluid exhaust pipe arranged between the core shaft 134 and the outer tube 133 to allow fluid exhaustion from the double layered balloon. The distal end of the core shaft 134 extending out of the double layered balloon 110 is provided with a soft tip 135. The soft tip 135 is made of a soft material to avoid damages to tissues. Preferably, a radiopaque marker 136 is disposed at the distal end of the core shaft 134, which may be made of a metallic, radiopaque material. During operation, the operator can confirm the position of the double layered balloon 110 relative to the outer sheath via the radiopaque marker 136 using an imaging device.

Further, present application also provides an electrophysiology system including the balloon catheter 100, an ablation energy output device 200 and control device 300. The ablation energy output device 200 is in fluid communication with the balloon catheter 100 so as to supply the balloon catheter 100 with an ablation medium. In some embodiments, the control device 300 is connected to the ablation energy output device 200, which is in turn connected to the balloon catheter 100. In other embodiments, the control device 300 may be connected to each of the ablation energy output device 200 and the balloon catheter 100. In still other embodiments, the control device 300 may be integrated along with the ablation energy output device 200 within a single unit. However, the present application is not limited thereto.

The control device 300 is configured to control the ablation energy output device 200 to adjust a temperature of the ablation medium (e.g., the temperature of the cryogenic liquid) based on temperature information detected by the temperature measuring element 120 so as to maintain an the surface temperature of the double layered balloon within a predetermined ablation temperature range. Suitable applications of the electrophysiology system may include, but are not limited to, cryoablation of a target tissue. Non-limiting examples of the target tissue may include the heart or a renal artery.

Figure 9:
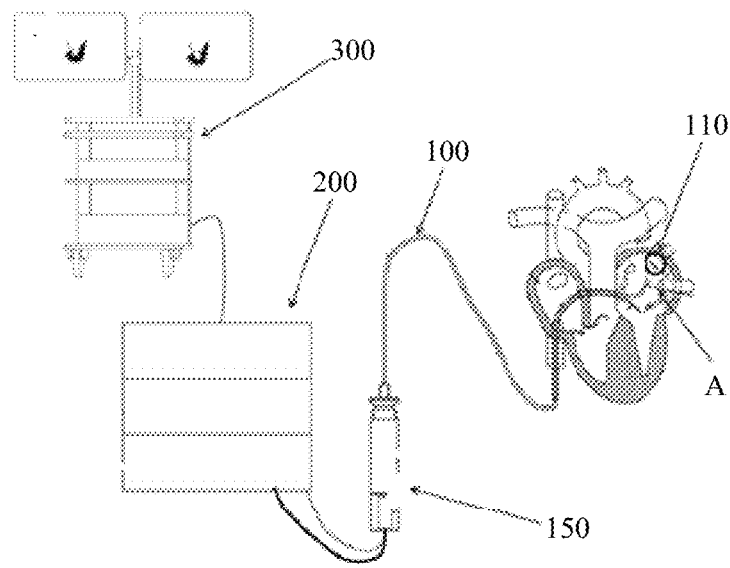
FIG. 9 is a schematic diagram of the cardiac ablation performed by an electrophysiology system according to an embodiment of the present application.
Figure 10:
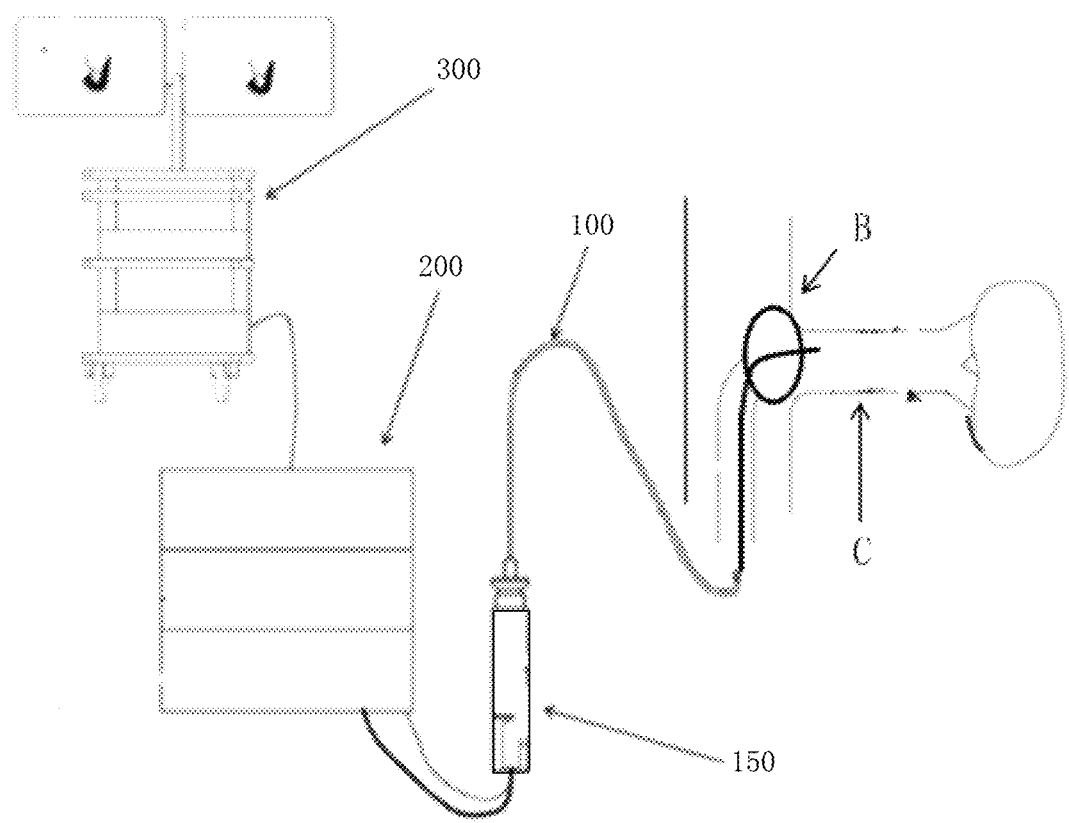
FIG. 10 is a schematic diagram of the renal artery ablation performed by an electrophysiology system according to an embodiment of the present application.

For example, as shown in FIG. 9, the electrophysiology system may be applied to cardiac therapy, in which the balloon catheter 100 is inserted into the heart using an interventional technique in order to perform ablation on the pulmonary vein A for treating a cardiac arrhythmia. Or, as shown in FIG. 10, the electrophysiology system may also be applied to the renal artery, in which the balloon catheter 300 is placed at the renal artery ostium B using an interventional technique to perform ablation of the renal artery C for adjusting blood pressure of the renal artery.

Figure 8:
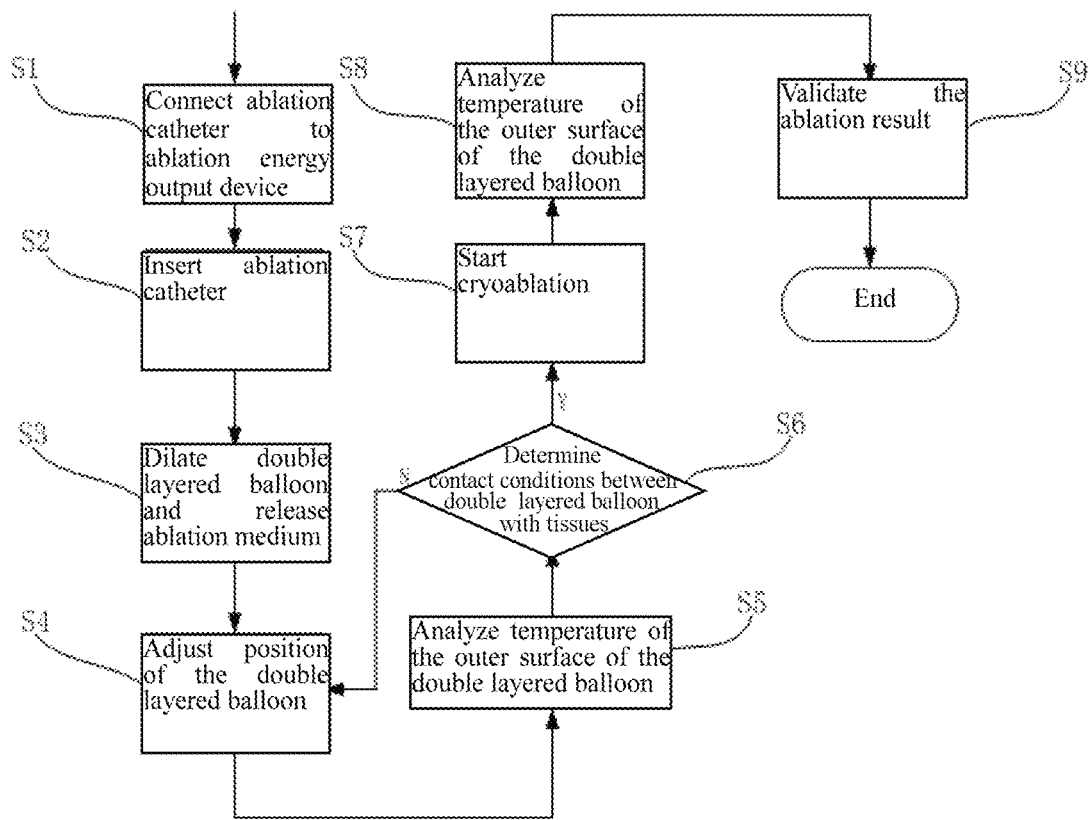
FIG. 8 shows a flowchart of a procedure performed by an electrophysiology system according to an embodiment of the present application.

Further, taking the cryoablation process of pulmonary vein as an example, the working principle of the electrophysiology system is illustrated in greater detail below with reference to FIGS. 8 and 9.

S1: Connecting the control handle 150 of the balloon catheter 100 to the ablation energy output device 200.

S2: Inserting the balloon catheter 100 into the target tissue to be ablated, such as the cylindrical tissue in the cardiac chamber, particularly the pulmonary vein orifice.

S3: Dilating the double layered balloon 110 and releasing the ablation medium (i.e., the cryogenic liquid) towards the double layered balloon 110.

S4: Adjusting the position of the double layered balloon 110 in the cylindrical tissue.

S5: Analyzing temperature of the outer surface of the double layered balloon 110 based on the temperature information detected by the plurality of temperature measuring elements 120.

S6: Determining contact conditions of the double layered balloon 110 with the cylindrical tissue. If desirable contact has been achieved between the double layered balloon 110 and the cylindrical tissue, the process proceeds to the next step. Otherwise, it returns back to S4.

S7: Starting cryoablation.

S8: Determining the ablation effect by analyzing temperature of the outer surface of the double layered balloon 110 based on the temperature information detected by the plurality of temperature measuring elements 120

S9: Validating the ablation result.

S10: Ending the ablation procedure.

In the procedure, the control device 300 analyzes and determines contact conditions between the double layered balloon 110 and the target tissue based on temperature information detected by the balloon catheter 100 and controls, on the basis of the analysis and determination, the ablation energy output device 200 to adjust an ablation temperature of the ablation medium.

In one embodiment, the control device 300 particularly includes a refrigeration control unit. The ablation energy output device 200 in particular includes a refrigeration unit, a fluid source and a fluid outlet channel. The fluid source communicates with the fluid outlet channel so as to allow a fluid to be output from the fluid source to the balloon catheter 100 through the fluid outlet channel. For example, the fluid outlet channel is connected to the fluid inlet interface 152 on the control handle 150 so as to introduce the ablation medium to the balloon catheter 100. The refrigeration unit is provided on the fluid outlet channel in order to refrigerate the fluid flowing through the fluid outlet channel. The refrigeration unit may be a compressor or another type of refrigeration device, and the present application is not limited in this regard. The refrigeration unit is communicatively coupled to the refrigeration control unit so as to control operation of the refrigeration unit by the refrigeration control unit. More specifically, the refrigeration control unit controls the refrigeration unit to work based on a received command of the cryoablation, so as to supply the cryogenic liquid to the balloon catheter 100 through the fluid outlet channel. In embodiments of the present application, a cryoablation button may be provided on the control handle 150, or a computer interface. The command of the cryoablation is sent to the refrigeration control unit 110 once the cryoablation button is launched by the operator.

The computer interface may be provided on the control device 300 or on the ablation energy output device 200. As a non-limiting example, the refrigeration control unit may send the refrigeration unit a refrigeration signal and the refrigeration unit starts to refrigerate based on the received refrigeration signal.

Further, during the cryoablation process, the refrigeration control unit controls, based on temperature information fed back by the plurality of temperature measuring elements 120, the refrigeration unit to adjust its refrigeration temperature, so as to maintain the balloon's outer surface temperature within a predetermined cryoablation temperature range.

Figure 11:
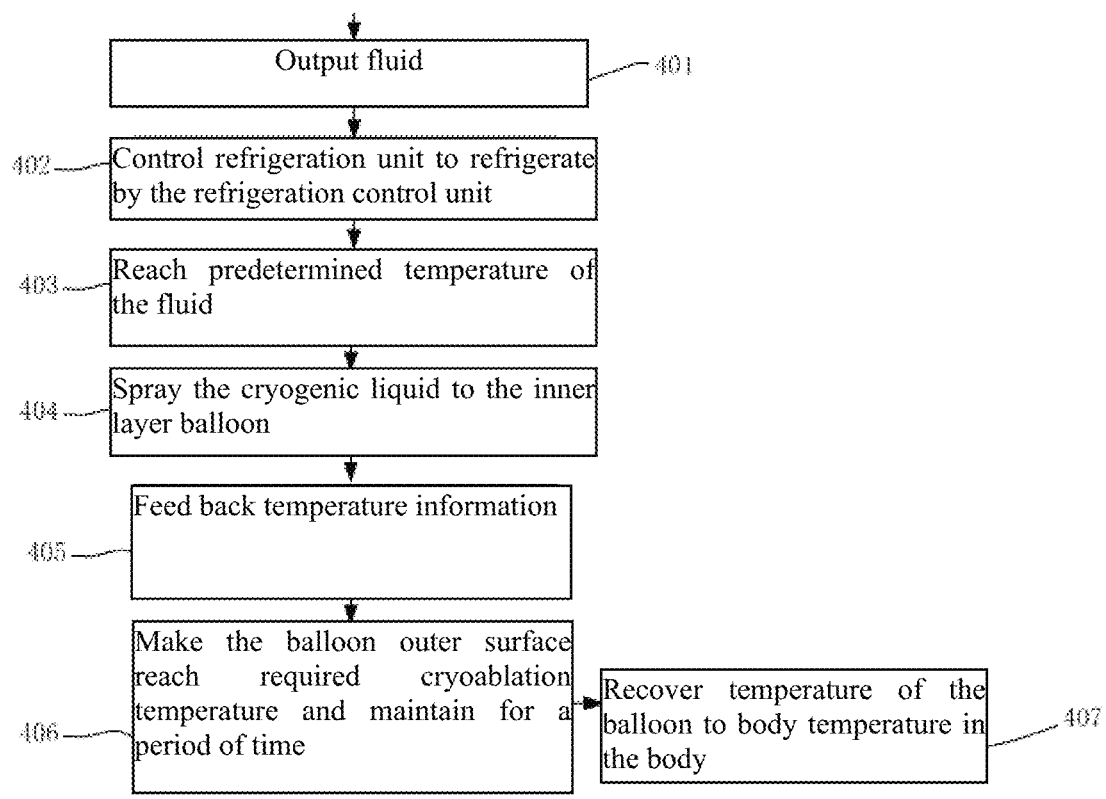
FIG. 11 shows a flowchart of a cryoablation procedure performed by an electrophysiology system according to an embodiment of the present application.

More particularly, as shown in FIG. 11, a cryoablation process performed by the electrophysiology system includes the following steps:

401: Outputting a fluid from the fluid source to the fluid outlet channel.

402: Controlling, by the refrigeration control unit, the refrigeration unit to refrigerate.

403: Refrigerating the fluid to a predetermined temperature;

404: Spraying the cryogenic liquid to the inner layer balloon. Actually, steps 401, 402, 403 and 404 can be carried out simultaneously so that the cryogenic liquid is sprayed onto an inner surface of the balloon at the beginning of the refrigeration.

405: Controlling, by the refrigeration control unit, refrigeration temperature of the refrigeration unit in real time based on temperature information fed back by the temperature measuring elements 120 during the refrigeration.

406: Ending the process after a required cryoablation temperature (e.g., from −40° C. to −60° C.) has been reached at the balloon outer surface and maintained for a period of time (e.g., 120-180 seconds).

Once a cycle of the cryoablation process is completed, the operator determines whether another cryoablation cycle is necessary based on the actual effect of cryoablation. However, it would be appreciated that, the balloon needs to naturally recover to body temperature in the body after each ablation cycle, so that the subsequent ablation cycle can be performed (step 407).

At last, the preferred embodiments of the present invention are as described above, but the scope of the present application is not limited to the above embodiments. For example, the temperature measuring element of present application may also be implemented as an optical fiber or a flexible printed sensor. Although these sensors may also be physically absorbed to the balloon surface via the adsorption element and do not restrain expansion and contraction of the balloon, these sensors manifest a poor use in effect compared with the linear-shaped temperature measuring element due to the sensors themselves. Additionally, the temperature sensing component may also be secured using soft non-metallic wires. For example, at least one braided knot is formed on the balloon surface, and the temperature sensing component is trapped in the braided knot.

The above description is merely a few preferred embodiments of present application and is not intended to limit the scope of present application in any sense. Any changes and modifications made by those of ordinary skill in the art based on the above teachings fall within the scope as defined in the appended

What is claimed is:

1. A balloon catheter, comprising:
    a catheter body;
    a double layered balloon disposed at a distal end of the catheter body, the double layered balloon comprising an inner layer balloon and an outer layer balloon covering the inner layer balloon;
    at least one temperature measuring element disposed within a space between the inner and outer layer balloons; and
    at least one adsorption element physically adsorbing and connecting both the temperature measuring element and the inner or outer layer balloon, so as to attach the temperature measuring element to the inner or outer layer balloon,
    wherein the adsorption element is displaceable relative to the inner or outer layer balloon to which the adsorption element is attached when the double layered balloon is deformed and also allows the temperature measuring element to displace relative to the inner or outer layer balloon to which the adsorption element is attached, and
    wherein when the adsorption element physically adsorbs and connects the inner layer balloon, the adsorption element covers an entire surface of the temperature measuring element that is away from the inner layer balloon in an axial direction of the double layered balloon, or wherein when the adsorption element physically adsorbs and connects the outer layer balloon, the adsorption element covers an entire surface of the temperature measuring element that is away from the outer layer balloon in an axial direction of the double layered balloon,
    wherein the adsorption element has a thickness of 100 μm or less and a width ranging from 0.2 mm to 3.0 mm.

2. The balloon catheter of claim 1, wherein the adsorption element is a physical adsorption element that is connected with the temperature measuring element via physical adsorption so as to allow the temperature measuring element to displace relative to the adsorption element when the double layered balloon is deformed, and is simultaneously connected with the inner or outer layer balloon via physical adsorption so as to allow the adsorption element to displace relative to the inner or outer layer balloon to which the adsorption element is attached when the double layered balloon is deformed and also to allow the temperature measuring element to displace relative to the inner or outer layer balloon to which the adsorption element is attached.

3. The balloon catheter of claim 2, wherein a maximum displacement of the adsorption element relative to the inner or outer layer balloon to which the adsorption element is attached when the double layered balloon is deformed does not exceed 15% of an outer diameter of the double layered balloon in an expanded configuration.

4. The balloon catheter of claim 2, wherein the adsorption element comprises a base and a physical adsorption layer provided on the base, and
    wherein a first part of the physical adsorption layer physically adsorbs the temperature measuring element, and a second part of the physical adsorption layer physically adsorbs one of the inner and outer layer balloons, the base configured to prevent the physical adsorption layer from adsorbing the other one of the inner and outer layer balloons.

5. The balloon catheter of claim 4, wherein the physical adsorption layer is made of a soft gel-like material that does not change its performance status before and after use.

6. The balloon catheter of claim 5, wherein the material of the physical adsorption layer is silicone or a hydrogel, and wherein the base is a film made of a macromolecular material, and the physical adsorption layer is coated on a surface of the film.

7. The balloon catheter of claim 1, wherein at least one end of the adsorption element is fixed to one end of the double layered balloon.

8. The balloon catheter of claim 7, wherein one end of the adsorption element is fixed to a proximal end of the double layered balloon, and the other end of the adsorption element is fixed to a distal end of the double layered balloon, and wherein a portion of the adsorption element between the proximal and distal ends of the double layered balloon adsorbs and connects the temperature measuring element and simultaneously adsorbs and connects the inner or outer layer balloon, and
wherein a length of the adsorption element is greater than a length of an unilateral contour line along the direction from the proximal to the distal ends of the double layered balloon in an expanded configuration.

9. The balloon catheter of claim 1, wherein the adsorption element has a width that is greater than or equal to a maximum width of the temperature measuring element, so that the temperature measuring element is not exposed outside the adsorption element in its width direction.

10. The balloon catheter of claim 1, wherein the temperature measuring element comprises two opposite ends and a main body between the two opposite ends,
wherein at least one end of the temperature measuring element is fixed to one end of the double layered balloon, and at least part of the main body of the temperature measuring element is attached to the inner or outer layer balloon by the adsorption element.

11. The balloon catheter of claim 1, wherein the temperature measuring element is a linear-shaped temperature sensor that has at least one end fixed to one end of the double layered balloon and is arranged along a direction from a proximal end of the double layered balloon to a distal end of the double layered balloon.

12. The balloon catheter of claim 11, wherein the adsorption element extends from the proximal to the distal ends of the double layered balloon so as to attach an entirety of the linear-shaped temperature sensor to the inner or outer layer balloon.

13. The balloon catheter of claim 12, wherein the adsorption element is a long strip in shape.

14. The balloon catheter of claim 11, wherein a portion of the temperature measuring element located between the proximal and distal ends of the double layered balloon are in an untensioned configuration when the double layered balloon does not expand, and wherein a length of the temperature measuring element in a stretched configuration is greater than a length of an unilateral contour line along the direction from the proximal to the distal ends of the double layered balloon in the expanded configuration, or wherein the linear-shaped temperature sensor is a thermocouple temperature sensor or thermistor temperature sensor.

15. The balloon catheter of claim 11, wherein the temperature measuring element comprises a first wire, a second wire and a temperature sensing component, the first and second wires coupled to each other and arranged in a crossover configuration, the temperature sensing component disposed between the first and second wires, the temperature sensing component configured to convert temperature information to electrical information, the first and second wires configured to transmit the electrical information,
wherein the temperature sensing component is attached to the inner or outer layer balloon via the adsorption element and/or at least partial segments of at least one of the first and second wires are attached to the inner or outer layer balloon by the adsorption element.

16. The balloon catheter of claim 1, wherein the catheter body comprises an outer tube and a core shaft disposed in the outer tube, a distal end of the core shaft extending out of the outer tube, wherein the core shaft is connected to a distal end of the double layered balloon, and the outer tube is connected to a proximal end of the double layered balloon.

17. The balloon catheter of claim 16, wherein the catheter body further comprises a fluid transfer pipe disposed between the core shaft and the outer tube, and the fluid transfer pipe is provided thereon fluid spraying orifices towards an surface of the inner layer balloon for spraying a cryogenic liquid into an interior of the inner layer balloon, the fluid spraying orifices arranged within a distal hemisphere of the double layered balloon.

18. An electrophysiology system comprising an ablation energy output device, a control device and the balloon catheter of claim 1, wherein the ablation energy output device is in communication with the balloon catheter to provide the balloon catheter with an ablation medium, and the control device is configured to control the ablation energy output device to adjust a temperature of the ablation medium based on temperature information detected by the temperature measuring element so as to maintain a temperature of a surface of the double layered balloon within a predetermined ablation temperature range.

* * * * *